United States Patent
Furusawa et al.

(10) Patent No.: US 6,664,213 B1
(45) Date of Patent: Dec. 16, 2003

(54) LIQUID PESTICIDE COMPOSITION

(75) Inventors: Hiroyuki Furusawa, Funabashi (JP); Mamoru Kobayashi, Funabashi (JP); Shigeo Hattori, Funabashi (JP); Hiromu Kobayashi, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/048,567

(22) PCT Filed: Aug. 16, 2000

(86) PCT No.: PCT/JP00/05481

§ 371 (c)(1), (2), (4) Date: Feb. 20, 2002

(87) PCT Pub. No.: WO01/13724

PCT Pub. Date: Mar. 1, 2001

(30) Foreign Application Priority Data

Aug. 19, 1999 (JP) ............................................. 11-232163
Jul. 18, 2000 (JP) ....................................... 2000-217642

(51) Int. Cl.$^7$ ............................................... A01N 25/30
(52) U.S. Cl. ...................... 504/215; 504/235; 504/362; 514/772; 514/975
(58) Field of Search ................................. 504/362, 215, 504/235; 514/772, 975

(56) References Cited

U.S. PATENT DOCUMENTS 5,078,782 A    1/1992  Nielsen et al. ................. 71/100
5,428,000 A  * 6/1995  Innami et al. ............... 504/104

FOREIGN PATENT DOCUMENTS

| EP | 0 357 149 A2 |   | 3/1990 |
| EP | 0 968 649 A1 |   | 1/2000 |
| JP | 5-163106 | * | 6/1993 |
| JP | A 9-278605 |   | 10/1997 |
| WO | WO 97/22247 |   | 6/1997 |
| WO | WO 99/09822 |   | 3/1999 |

OTHER PUBLICATIONS

Green, "Varying Surfactant Type Changes Quizalofop–P Herbicidal Activity", Weed Technology, 1997 vol. 11, pp. 298–302.

* cited by examiner

Primary Examiner—S. Mark Clardy
(74) Attorney, Agent, or Firm—Oliff & Berridge, PLC

(57) ABSTRACT

A novel liquid pesticide composition comprising a pesticidally active ingredient and a polyoxyethylene alkyl ether which has the following features (a) and (b): (a) an HLB value of 6 to 13.5; and (b) a content of 10 to 50 wt % based on the liquid pesticide composition.

20 Claims, No Drawings

LIQUID PESTICIDE COMPOSITION

This application has been filed under 35 USC 371 as the national stage of international application PCT/JP00/05481, filed Aug. 16, 2000.

TECHNICAL FIELD

The present invention relates to a liquid pesticide composition having a high content of specific polyoxyethylene alkyl ether and an improved biological effect.

BACKGROUND ART

It is known that when various nonionic surfactants are added to a spray solution of an emulsifiable concentrate of Quizalofop-ethyl (general term), a polyoxyethylene alkyl ether improves a herbicidal effect better than other surfactants (Weed Technology, 11, 298–302 (1997)) It is also known that the herbicidal effect of a solid herbicide formulation is improved by adding 0.01 to 0.5 wt % of a polyoxyethylene alkyl ether to a spray solution (EP0968649A1). It is further known that a compound prepared by adding ethylene oxide to a higher alcohol having 13 carbon atoms in an amount of 5 to 8 moles on the average is used as a pesticide spreader (Japanese Laid-open Patent Application No. 9-278605).

DISCLOSURE OF INVENTION

The present inventors have conducted intensive studies and have found that the biological effect of a pesticidally active ingredient is greatly improved by containing a polyoxyethylene alkyl ether in a liquid pesticide composition in high concentration. They have also found that when a polyoxyethylene alkyl ether having a specific HLB value is used, a homogeneous liquid pesticide composition having excellent storage stability can be prepared although a homogeneous liquid pesticide composition having excellent storage stability may not be prepared when the polyoxyethylene alkyl ether is contained in a liquid pesticide composition in high concentration.

That is, the present invention relates to the following liquid pesticide compositions [1] to [11] (to be referred to as "compositions of the present invention" hereinafter).

[1] a liquid pesticide composition comprising a pesticidally active ingredient and a polyoxyethylene alkyl ether which has the following features (a) and (b):
 (a) an HLB value of 6 to 13.5 and (b) a content of 10 to 50 wt % based on the liquid pesticide composition.
[2] a liquid pesticide composition comprising a pesticidally active ingredient and a polyoxyethylene alkyl ether which has the following features (a) and (b):
 (a) an HLB value of 8 to 13.5 and (b) a content of 10 to 50 wt % based on the liquid pesticide composition.
[3] a liquid pesticide composition comprising a pesticidally active ingredient and a polyoxyethylene alkyl ether which has the following features (a) and (b):
 (a) an HLB value of 11 to 13.5 and (b) an content of 10 to 50 wt % based on the liquid pesticide composition.
[4] the liquid pesticide compositions [1] to [3], wherein the pesticidally active ingredient is a herbicide.
[5] the liquid pesticide composition [4], wherein the herbicide is a herbicide having foliar treating activity.
[6] the liquid pesticide composition [5], wherein the herbicide having foliar treating activity is a phenoxypropionic acid herbicide.
[7] the liquid pesticide composition [6], wherein the phenoxypropionic acid herbicide is Quizalofop-ethyl.
[8] the liquid pesticide composition [5], wherein the herbicide having foliar treating activity is a sulfonylurea herbicide.
[9] the liquid pesticide composition [8], wherein the sulfonylurea herbicide is Halosulfuron-methyl.
[10] the liquid pesticide compositions [1] to [3] which are aqueous suspension formulations.
[11] the liquid pesticide compositions [1] to [3] which are emulsifiable concentrates.

The content of the polyoxyethylene alkyl ether in the composition of the present invention must be 10 to 50 wt % to fully improve the biological effect of the pesticidally active ingredient. With a view to reducing the viscosity of the liquid pesticide composition to improve handling properties, it is preferably 30 wt % or less. With a view to further stabilizing the biological effect, it is preferably 15 wt % or more. Therefore, the content of the polyoxyethylene alkyl ether is preferably 10 to 30 wt %, more preferably 15 to 30 wt %.

It is known that polyoxyethylene alkyl ethers have different HLB (Hydrophile-Lipophilic Balance) values according to the type of the alkyl group of an alcohol moiety and the molar ethylene oxide (EO) content. The HLB value is an index of the hydrophilic nature of a surfactant proposed by Griffin. The HLB value of a polyoxyethylene alkyl ether can be obtained from the following Griffin equation.

HLB value=[(molecular weight of hydrophilic moiety)/(molecular weight of surfactant)]×20

The HLB value of a paraffin having no hydrophilic group is 0, the HLB value of polyethylene glycol having no hydrophobic group is 20, and the HLB value of a polyoxyethylene alkyl ether ranges from 0 to 20.

It was found from the research conducted by the present inventors that when a polyoxyethylene alkyl ether having an HLB value of more than 13.5 was contained in a liquid pesticide composition in an amount of 10 to 50 wt %, the sedimentation of a visible insoluble product was observed and a homogeneous liquid pesticide composition having excellent storage stability could not be prepared whereas when a polyoxyethylene alkyl ether having an HLB value of 6 to 13.5 was contained in a liquid pesticide composition in an amount of 10 to 50 wt %, a homogeneous liquid pesticide composition having excellent storage stability could be prepared.

Therefore, the HLB value of the polyoxyethylene alkyl ether used in the present invention must be 6 to 13.5. With a view to further improving the biological effect, the HLB value is preferably 8 to 13.5, more preferably 11 to 13.5.

The mean molar ethylene oxide (EO) content of the polyoxyethylene alkyl ether having an HLB value of 6 to 13.5 used in the present invention is preferably 4 to 20, more preferably 4 to 12, much more preferably 6 to 12. The alkyl group of an alcohol moiety of the polyoxyethylene alkyl ether having an HLB value of 6 to 13.5 used in the present invention may be either linear or branched and the number of carbon atoms of the alkyl moiety is preferably 10 to 18., more preferably 10 to 16, much more preferably 12 to 14.

The composition of the present invention may comprise a surfactant other than the polyoxyethylene alkyl ether, as exemplifiedby the following surfactants (A), (B), (C), (D) and (E).

(A) nonionic surfactants:
 (A-1) polyethylene glycol type surfactants: adducts of alkyl naphthols with ethylene oxide, polyoxyethylene (mono- or di-) (C8~C12 alkyl)phenyl ethers, formalin condensates of polyoxyethylene ((mono- or di-)

C8~C12 alkyl)phenyl ethers, polyoxyethylene (mono-, di- or tri-)phenyl phenyl ethers, polyoxyethylene (mono-, di- or tri-)benzyl phenyl ethers, polyoxypropylene (mono-, di- or tri-)benzyl phenyl ethers, polyoxyethylene (mono-, di- or tri-)styryl phenyl ethers, polyoxypropylene (mono-, di- or tri-)styryl phenyl ethers, polyoxyethylene (mono-, di- or tri-)styryl phenyl ether polymers, polyoxyethylene polyoxypropylene block polymers, (C12~C18alkyl) polyoxyethylene polyoxypropylene block polymer ethers, (C8~C12alkyl)phenyl polyoxyethylene polyoxypropylene block polymer ethers, polyoxyethylene bisphenyl ethers, polyoxyethylene resin acid esters, polyoxyethylene (C12~C18 fatty acid) monoesters, polyoxyethylene (C12~C18 fatty acid) diesters, polyoxyethylene sorbitan (C12~C18 fatty acid) esters, adducts of glycerol fatty acid esters with ethylene oxide, adduct of castor oil with ethylene oxide, adduct of hardened castor oil with ethylene oxide, adducts of (C12~C18alkyl) amines with ethylene oxide, adducts of (C12~C18 fatty acid) amides with ethylene oxide and the like.

(A-2) polyhydric alcohol type surfactants: glycerol fatty acid esters, polyglycerin fatty acid esters, pentaerythritol fatty acid esters, sorbitol (C12~C18 fatty acid) esters, sorbitan (C12~C18 fatty acid) esters, sucrose fatty acid esters, polyhydric alcohol alkyl ethers, fatty acid alkanol amides and the like.

(A-3) acetylene type surfactants: acetylene glycol, acetylene alcohols, adduct of acetylene glycol with ethylene oxide, adducts of acetylene alcohols with ethylene oxide and the like.

(A-4) other surfactants: alkyl glycosides and the like (B) anionic surfactants (B-1) carboxylic acid type surfactants: carboxylic acids such as polyacrylic acid, polymethacrylic acid, polymaleic acid, copolymer of maleic acid and olefins (such as isobutylene and diisobutylene), copolymer of acrylic acid and itaconic acid, copolymer of methacrylic acid and itaconic acid, copolymer of maleic acid and styrene, copolymer of acrylic acid and methacrylic acid, copolymer of acrylic acid and methyl acrylate, copolymer of acrylic acid and vinyl acetate, copolymer of acrylic acid and maleic acid, N-methyl-(C12~C18 fatty acid) sarcosinates, resin acid and C12~C18 fatty acids, and salts thereof.

(B-2) sulfate type surfactants: sulfates such as (C12~C18 alkyl) sulfates, polyoxyethylene (C12~C18 alkyl) ether sulfates, polyoxyethylene ( (mono- or di-) C8~C12 alkyl)phenyl ether sulfates, sulfates of polyoxyethylene ((mono- or di-) C8~C12alkyl)phenyl ether polymers, polyoxyethylene (mono-, di- or tri-)phenyl phenyl ether sulfates, polyoxyethylene (mono-, di- or tri-)benzyl phenyl ether sulfates, polyoxyethylene (mono-, di- or tri-)styryl phenyl ether sulfates, sulfates of polyoxyethylene (mono-, di- or tri-) styryl phenyl ether polymers, sulfates of polyoxyethylene polyoxypropylene block polymers, sulfonated oil, sulfated fatty acid esters, sulfated fatty acids and sulfated olefins, and salts thereof.

(B-3) sulfonic acid type surfactants: sulfonic acids such as (C12~C22 paraffin)sulfonic acids, (C8~C12alkyl) benzenesulfonic acids, formalin condensates of (C8~C12alkyl)benzenesulfonic acids, formalin condensate of cresolsulfonic acid, (α-olefin(C14~C16)) sulfonic acids, di(C8~C12 alkyl)sulfosuccinic acids, lignin sulfonic acid, polyoxyethylene ((mono- or di-) C8~C12alkyl)phenyl ether sulfonic acids, polyoxyethylene (C12~C18alkyl)ether sulfosuccinic acid half esters, naphthalenesulfonic acid, ((mono- or di-) C1~C6alkyl) naphthalenesulfonic acids, formalin condensate of naphthalenesulfonic acid, formalin condensates of ((mono- or di-)C1~C6alkyl) naphthalenesulfonic acids, formalin condensate of creosote oil sulfonic acid, (C8~C12alkyl)diphenyl ether disulfonic acids, Igepon T (trade name), polystyrene sulfonic acid and copolymer of styrenesulfonic acid and methacrylic acid, and salts thereof.

(B-4) phosphate type surfactants: phosphates such as (C8~C12alkyl)phosphates, polyoxyethylene (C12~C18alkyl) ether phosphates, polyoxyethylene ((mono- or di-) C8~C12alkyl) phenyl ether phosphates, phosphates of polyoxyethylene ((mono-, di- or tri-) C8~C12alkyl)phenyl ether polymers, polyoxyethylene (mono-, di- or tri-)phenyl phenyl ether phosphates, polyoxyethylene (mono-, di- or tri-)benzyl phenyl ether phosphates, polyoxyethylene (mono-, di- or tri-)styryl phenyl ether phosphates, phosphatesofpolyoxyethylene (mono-, di- or tri-)styryl phenyl ether polymers, phosphates of polyoxyethylene polyoxypropylene block polymers, phosphatidyl choline, phosphatidyl ethanolimine and condensed phosphoric acid (such as tripolyphosphoric acid), and salts thereof.

The salts in (B-1) to (B-4) above include alkali metals (such as lithium, sodium and potassium), alkali earth metals (such as calcium and magnesium), ammonium and various amines (such as alkylamines, cycloalkylamines and alkanolamines).

(C) cationic surfactants: alkylamine salts, alkyl quaternary ammonium salts and the like.

(D) amphoteric surfactants: betain type surfactants, amino acid type surfactants and the like.

(E) other surfactants: organosilicone surfactants, organofluorine surfactants and the like.

The pesticidally active ingredient used in the composition of the present invention is not particularly limited but preferably a herbicide. Examples of the herbicide include sulfonylurea herbicides such as Amidosulfuron (general term), Azimsulfuron (general term), Bensulfuron-methyl (general term), Chlorimuron-ethyl (general term), Chlorsulfuron (general term), Cinosulfuron (general term), Cyclosulfamuron (general term), Ethametsulfuron-methyl (general term), Ethoxysulfuron (general term), Flazasulfuron (general term), Flupyrsulfuron-methyl (general term), Flupyrsulfuron-methyl-sodium (general term), Halosulfuron-methyl (general term), Imazosulfuron (general term), Metsulfuron-methyl (general term), Nicosulfuron (general term), Oxasulfuron (general term), Primisulfuron-methyl (general term), Prosulfuron (general term), Pyrazosulfuron-ethyl (general term), Rimsulfuron (general term), Sulfometuron-methyl (general term), Sulfosulfuron (general term), Thifensulfuron-methyl (general term), Triasulfuron (general term), Tribenuron-methyl (general term) and Triflusulfuron-methyl (general term); phenoxypropionic acid herbicides such as Clodinafop-propargyl (general term), Cyhalofop-butyl (general term), Diclofop-methyl (general term), Difenopenten-methyl (general term), Fenoxaprop-ethyl (general term), Fluazifop-buthyl (general term), Haloxyfop (general term), Haloxyfop-methyl (general term), Isoxapyrifop (general term), Propaquizafop (general term), Quizalofop-ethyl (general term), Quizalofop-tefuryl (general term) and Fenthiaprop-ethyl (general term); and Chlorbromuron (general term), Chlorotoluron (general term), Dimefuron (general term), Diuron (general term), Fenuron (general term), Fluometuron (general term), Isoproturon (general term), Isouron (general term), Linuron (general term), Metabenzthiazuron (general term), Methyldymuron (general term), Metobenzuron (general term), Metobromuron (general term), Monolinuron (general term), Neburon (general term), Metoxuron (general term), Siduron (general term), Tebuthiuron (general term), Benzthiazuron (general term), Chlorpropham (general term), Desmedipham (general term), Dimepiperate (general term), Karbutilate (general term), Phenisopham (general term), Phenmedipham (general term), Propham (general term), swep (general term), Cycloate (general term), Diallate (general term), EPTC (general term), Esprocarb (general term), Molinate (general term), Orbencarb (general term), Pebulate (general term), Prosulfocarb (general term), Pyributicarb (general term), Thiobencarb (general term), Thiocarbazil (general term), Triallate (general term), Vernolate (general term), Chlorprocarb (general term), Chlorbupham (general term), Bispyribac (general term), Bispyribac-sodium (general term), Pyriminobac-methyl (general term), Pyrithiobac (general term), Pyrithiobac-sodium (general term), Pyribenzoxim (general term), Imazamathabanz (general term), Imazamathabanz-methyl (general term), Imazamox (general term), Imazapyr (general term), Imazaquin (general term), Imazaquin-ammonium (general term), Imazethapyr (general term), Imazethapyr-ammonium (general term), 2-(4,5-dihydro-4-isopropyl-4-methyl-5-oxo-methylnicotinic acid (AC 263222), Cloransulam-methyl (general term), Diclosulam (XDE-564) (general term), Flumetsulam (general term), Metosulam (general term), Benfuresate (general term), Ethofumesate (general term), Alachlor (general term), Acetochlor (general term), Butachlor (general term), Dimethachlor (general term), Dimethenamid (general term), Metazachlor (general term), Metolachlor (general term), Pretilachlor (general term), Propachlor (general term), Propisochlor (general term), Thenylchlor (general term), Ametryn (general term), Atrazine (general term), Cyanazine (general term), Desmetryn (general term), Dimethametryn (general term), Hexazinon (general term), Metamitron (general term), Metribuzin (general term), Prometon (general term), Prometryn (general term), Propazine (general term), Simazine (general term), Simetryne (general term), Terbumeton (general term), Terbutryn (general term), Terbutylazin (general term), Trietazine (general term), Alloxydim (general term), Butroxydim (general term), Clethodim (general term), Cycloxydim (general term), Sethoxydim (general term), Tralkoxydim (general term), Tepraloxydim (BAS 620H) (general term), Acifluorfen (general term), Acifluorfen-sodium (general term), Aclonifen (general term), Bifenox (general term), Chlomethoxyfen (general term), Chlornitrofen (general term), Ethoxyfen-ethyl (HC-252) (general term), Fluoroglycofen-ethyl (general term), Fomesafen (general term), Halosafen (general term), Lactofen (general term), Oxyfluorfen (general term), methyl [[[1-[5(2-chloro-4-(trifluoromethyl) phenoxy)-2-nitrophenyl]-2-methoxyethylidene]amino]oxy]acetate (AKH-7088), Azafenidin (general term), Carfentrazone-ethyl (general term), Flumiclorac-penthyl (general term), Flumioxazin (general term), Flumipropyn (general term), Flupropacil (general term), Fluthiacet-methyl (general term), Oxadiargyl (general term), Oxadiazon (general term), Pentoxazone (general term), Pyraflufen-ethyl (general term), Sulfentrazone (general term), Thidiazimin (SN-124085) (general term), Nipyraclofen (general term), Cinidon-ethyl (general term), Chlorphthalim (general term), Isoxaflutole (general term), Pyrazolynate (general term), Pyrazoxyfen (general term), Sulcotrione (general term), Benzofenap (general term), Fluthiamide (BAY FOE5043) (general term), Mefenacet (general term), Napropamide (general term), Bromacil (general term), Terbacil (general term), Bromoxynil (general term), Ioxynil (general term), Anilofos (general term), Bromobutide (general term), Cafenstrole (general term), Clomeprop (general term), Cumyluron (general term), Daimuron (general term), Etobenzanid (general term), Indanofan (general term), Naproanilide (general term), Fentrazamide (general term), Benfluralin (general term), Butralin (general term), Dinitramine (general term), Dinoterb (general term), DNOC (general term), Ethalfluralin (general term), Fluchloralin (general term), Oryzalin (general term), Pendimethalin (general term), Prodiamine (general term), Trifluralin (general term), Chloramben (general term), Chlorthal-dimethyl (general term), Dicamba (general term), Diflufenican (general term), Chloridazon (general term), Norflurazon (general term), Clopyralid (general term), Picloram (general term), 2,4-D (general term), 2,4-DB (general term), 2,4-DP (general term), MCPA (general term), MCPB (general term), MCPP (general term), Triclopyr (general term), Dithiopyl (general term), Fluroxypyr (general term), Thiazopyr (general term), Flupoxam (general term), Triazofenamide (general term), Acrolein (general term), Amitrole (general term), Asulam (general term), Bilanafos (general term), Diflufenzopyr (general term), Benazolin (general term), Benazolin-ethyl (general term), Bensulide (general term), Bentazone (general term), Bromofenoxim (general term), Butamifos (general term), Butylate (general term), Carbetamide (general term), Cinmethylin (general term), Clomazone (general term), Chlorthiamid (general term), Dalapon (general term), Dazomet (general term), Dichlobenil (general term), Difenzoquat (general term), Diphenamid (general term) Diquat (general term), Endothal (general term), Flamprop (general term), Flurenol (general term), Fluridone (general term), Fluorochloridone (general term), Flurtamone (general term), Fosamine (general term), Glufosinate (general term), Glyphosate (general term), Sulphosate (general term), Hydantocidin (general term), Isoxaben (general term), Lenacil (general term), Mefluidide (general term), Metam-sodium (general term), Metamitron (general term), Naptalam (general term), Paraquat (general term), Pentanochlor (general term), Perfluidone (general term), Piperophos (general term), Propanil (general term), Propyzamide (general term), Pyridate (general term), Quinclorac (general term), Quinmerac (general term), 2,3,6-TBA (general term), TCA (general term), Tebutam (general term), Triaziflam (general term), Tridiphane (general term) and the like.

Further, the herbicide is preferably is a herbicide having foliar treating activity, more preferably phenoxypropionic acid herbicide or sulfonylurea herbicide. Out of these, Quizalofop-ethyl and Halosulfuron-methyl are the most preferred.

These pesticidally active ingredients may be used alone or in admixture of two or more. When they are mixed together, the mixing ratio is arbitrary. Further, the content of the pesticidally active ingredient(s) is not particularly limited but the weight ratio of the pesticidally active ingredient to the polyoxyethylene alkyl ether is preferably 5:1 to 1:50, more preferably 5:1 to 1:10.

Quizalofop-ethyl is an optically active compound and it is known that Quizalofop-ethyl is ethyl=(R)-2-[4-(6-chloroquinoxalin-2-yloxy)phenoxy]propionate (to be referred to as "Quizalofop-p-ethyl" hereinafter) or ethyl=(S)-2-[4-(6-chloroquinoxalin-2-yloxy)phenoxy]propionate.

Further, it is known that Quizalofop-p-ethyl have an α type crystal form (low melting point crystal) which is a plate crystal form having a heat absorption peak at around 74° C. and a β type crystal form (high melting point crystal) which is a needle-like crystal form having a heat absorption peak at around 80° C. according to differential scanning calorimetry.

The two crystal forms of Quizalofop-p-ethyl are easily identified by powdery X-ray diffraction, differential scanning calorimetry or microscopic observation.

The features of the two crystal forms are shown below.

|  | Melting point | Crystal form | Characteristic X-ray diffraction peak |
| --- | --- | --- | --- |
| α type crystal | 74 to 76° C. | plate | $2\theta$ = 4.36, 8.68 |
| β type crystal | 80 to 82° C. | needle-like | $2\theta$ = 5.32, 6.38 |

Since the weight ratio of the α type crystal to the β type crystal is approximate to the area ratio of their heat absorption peaks measured by differential scanning calorimetry, the weight ratio of the a type crystal to the β type crystal can be obtained from the area ratio of their heat absorption peaks.

The method of obtaining Quizalofop-p-ethyl which contains β type crystals in a proportion of 80 wt % or more is not particularly limited but a method disclosed by Japanese Patent Publication No. 4-76721 may be used. Quizalofop-p-ethyl which contains β type crystals in a desired proportion can be obtained by the method.

When the composition of the present invention is an aqueous suspension formulation, Quizalofop-p-ethyl preferably contains β type crystals in a proportion of 80 wt % or more from the viewpoint of the storage stability of the obtained pesticide composition, more preferably 85 wt % or more, much more preferably 90 wt % or more.

The term "liquid pesticide composition" of the present invention means a pesticide composition which is liquid at normal temperature, such as an aqueous suspension formulation, emulsifiable concentrate (EC), soluble concentrate (SL) or microemulsion (ME). The term "aqueous suspension formulation" means a composition containing a pesticidally active ingredient dispersed uniformly in a water phase, such as a suspension concentrate (SC), emulsion oil in water (EW) or suspoemulsion (SE). The suspension concentrate is a formulation containing a solid pesticidally active ingredient dispersed in a water phase, the emulsion oil in water is a formulation prepared by emulsifying a liquid pesticidally active ingredient or a solution of a pesticidally active ingredient in organic solvent in a water phase, and the suspoemulsion is a mixed formulation of a suspension concentrate and emulsion oil in water.

Other adjuvants, which can be contained in the composition of the present invention, are as follows. In the case of an aqueous suspension formulation, a thickener, antifreezing agent, defoamer, bacteria and mildew proofing agent, pH modifier, coloring agent, organic solvent and the like may be used. In the case of an emulsifiable concentrate, a defoamer, pH modifier, coloring agent, organic solvent and the like may be used. In the case of a soluble concentrate, an antifreezing agent, defoamer, bacteria and mildew proofing agent, pH modifier, coloring agent and the like may be used. In the case of a microemulsion, an antifreezing agent, defoamer, bacteria and mildew proofing agent, pH modifier, coloring agent, co-solvent and the like may be used.

The thickener may be an organic or inorganic natural product, synthetic product or semi-synthetic product. Examples of the thickener include hetero polysaccharides such as xanthane gum, Welan gum and Rhamsan gum, water-soluble polymer compounds such as polyvinyl alcohols, polyvinylpyrrolidone, polyacrylic acid, sodium polyacrylate and polyacrylamides, cellulose derivatives such as methyl cellulose, carboxymethyl cellulose, carboxyethyl cellulose, hydroxyethyl cellulose and hydroxypropyl cellulose, smectite clay such as montmorillonite, saponite, hectorite, bentonite, Laponite and synthetic smectite, and the like. These thickeners may be used alone or in admixture of two or more. When the thickeners are mixed together, the mixing ratio is at one's option. The thickener may be added directly, or an aqueous dispersion of the thickener may be added. The amount of addition to the composition of the present invention is at one's option.

Examples of the antifreezing agent include ethylene glycol, diethylene glycol, propylene glycol and the like. The amount of addition to the composition of the present invention is at one's option.

Examples of the defoamer include a silicone emulsion and the like.

Various substances such as benzoic acid and salts thereof, Proxel GXL (ICI Co.) and Proxel XL-2 (ICI Co.) may be used as the bacteria and mildew proofing agent-.

The pH modifier is not particularly limited if it can control pH, as exemplified by inorganic acids such as hydrochloric acid, sulfuric acid, phosphoric acid, sulfonic acid and organic acid such as carboxylic acid, and salts and esters thereof. The amount of addition to the composition of the present invention is at one's option.

Examples of the organic solvent include aromatic. hydrocarbons such as xylene, alkylbenzenes (the alkyl moiety has C9, C10, etc.), phenylxylylethane and alkylnaphthalene (the alkyl moiety has C1,C3, etc.), aliphatic hydrocarbons such as machine oil, normal paraffin, isoparaffin and naphthene, mixtures of an aromatic hydrocarbon and an aliphatic hydrocarbon such as kerosene, alcohols such as ethanol, isopropanol, cyclohexanol and benzyl alcohol, polyhydric alcohols such as ethylene glycol, propylene glycol, diethylene glycol, hexylene glycol, polyethylne glycol and polypropylene glycol, ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether, ketones such as acetophenone, cyclohexanone and γ-butyrolactone, esters such as fatty acid methyl esters, succinic acid dialkyl esters, glutamic acid dialkyl esters, adipic acid dialkyl esters and phthalic acid dialkyl esters, acid amides such as N-alkyl pyrrolidone(the alkyl moiety has C1,C8,C12, etc.), fats and oils such as soybean oil, linseed oil, rape seed oil, coconut oil, cotton seed oil and castor oil, and dimethylsulfoxide. These organic solvent may be used alone or in admixture of two or more. When the organic solvents are mixed together, the mixing ratio is at one's option. The amount of addition to the composition of the present invention is at one's option.

The composition of the present invention can be produced by the following method.

A suspension concentrate of the composition of the present invention can be obtained by mixing a solid component contained in the composition of the present invention into water containing a surfactant, fine grinding it with a wet grinder such as a sand grinder, and adding and mixing other adjuvants such as a thickener, or by mixing a solid component contained in the composition of the present invention which has been finely ground with a dry grinder into water containing a surfactant and adding and mixing other adjuvants such as a thickener.

An emulsion oil in water of the composition of the present invention can be obtained by mixing a surfactant with a liquid pesticidally active ingredient or a solution of a solid pesticidally active ingredient in an organic solvent, gradually adding water under stirring, and then adding and mixing other adjuvants such as a thickener. Alternatively, it can be obtained by adding a liquid pesticidally active ingredient, surfactant and thickener into a water, and emulsifying and dispersing them with a disperser.

A suspoemulsion of the composition of the present invention can be obtained by mixing a suspension concentrate and an emulsion oil in water which have been prepared separately, by adding a mixture of a liquid pesticidally active ingredient and a surfactant dropwise to water and then dispersing a dry ground solid pesticidally active ingredient and other adjuvants such as a thickener into the water solution, or by emulsifying a liquid pesticidally active ingredient with a suspension concentrate obtained by the method described above.

An emulsifiable concentrate-of the composition of the present invention can be obtained by dissolving a pesticidally active ingredient and a surfactant in an organic solvent.

Best Mode for Carrying Out the Invention

Examples of the composition of the present invention and Comparative Examples of aqueous suspension formulations and emulsifiable concentrates used for comparison will be provided. "Parts" in Examples and Comparative Examples means "parts by weight". The present invention is not limited to these examples.

The viscosity of an aqueous suspension formulation was measured with a Brookfield type viscometer (Model DV-III of Brookfield Co.) and No. 2 rotor at a revolution of 30 rpm and a temperature of 25° C. and a concentrate of an aqueous suspension formulation was used as a measurement solution.

EXAMPLE 1

1.0 part of polyoxyethylene tristyrylphenyl ether phosphate was dissolved in 58.3 parts of water, and then to the solution 4.5 parts of dry ground Halosulfuron-methyl, 15.0 parts of a water dispersion containing 1% of Proxel GXL (trade name of Zeneca Co.) and 1% of Welan gum (of Kelco Biopolymers Co.), 1.0 part of citric acid monohydrate, 10.0 parts of propylene glycol, and 0.2 part of Nopco 8034L (trade name of San Nopco Ltd.) were dispersed in the order named, and further 10.0 parts of a polyoxyethylene alkyl ether (HLB: 12.1, the mean molar ethylene oxide(EO) content: 7, the alkyl moiety: branched alkyl having 12 to 14 carbon atoms) was added to obtain a homogeneous aqueous suspension formulation having excellent storage stability. The viscosity of the obtained aqueous suspension formulation was 296 mPaS.

EXAMPLE 2

1.0 part of polyoxyethylene tristyrylphenyl ether phosphate was dissolved in 53.3 parts of water, and then to the solution 4.5 parts of dry ground Halosulfuron-methyl, 10.0 parts of a water dispersion containing 1% of Proxel GXL (trade name of Zeneca Co.) and 1% of Welan gum (of Kelco Biopolymers Co.), 1.0 part of citric acid monohydrate, 10.0 parts of propylene glycol and 0.2 part of Nopco 8034L (trade name of San Nopco Ltd.) were dispersed in the order named, and further 20.0 parts of a polyoxyethylene alkyl ether (HLB: 12.1, the mean molar ethylene oxide(EO) content: 7, the alkyl moiety: branched alkyl having 12 to 14 carbon atoms) was added to obtain a homogeneous aqueous suspension formulation having excellent storage stability. The viscosity of the obtained aqueous suspension formulation was 278 mPaS.

Comparative Example 1

An attempt was made to prepare an aqueous suspension formulation in the same manner as in Example 1 except that the type of polyoxyethylene alkyl ether was changed to a polyoxyethylene alkyl ether having an HLB of 14, the mean molar ethylene oxide (EO) content of 11 and the alkyl moiety which is a linear alkyl having 14 to 15 carbon atoms. However, the sedimentation of a visible insoluble product was observed and a homogenous aqueous suspension formulation having high storage stability could not be prepared.

Comparative Example 2

An attempt was made to prepare an aqueous suspension formulation by the following method. 1.0 part of polyoxyethylene tristyrylphenyl ether phosphate was dissolved in 48.3 parts of water, and then to the solution 4.5 parts of dry ground Halosulfuron-methyl, 15.0 parts of a water dispersion containing 1% of Proxel GXL (trade name of Zeneca Co.) and 1% of Welan gum (of Kelco Biopolymers Co.), 1.0 part of citric acid monohydrate, 10.0 parts of propylene glycol and 0.2 part of Nopco 8034L (trade name of San Nopco Ltd.) were dispersed in the order named, and further 20.0 parts of a polyoxyethylene alkyl ether (HLB: 14, the mean molar ethylene oxide(EO) content: 11, the alkyl moiety: linear alkyl having 14 to 15 carbon atoms) was mixed with the dispersion. However, the sedimentation of a visible insoluble product was observed and a homogenous aqueous suspension formulation having high storage stability could not be prepared.

TABLE 1

Evaluation of prepared formulations

| | Polyoxyethylene alkyl ether | | Evaluation of |
| --- | --- | --- | --- |
| | Concentration in formulation | HLB | prepared formulations |
| Example 1 | 10 | 12.1 | ○ |
| Example 2 | 20 | 12.1 | ○ |
| Comparative Example 1 | 10 | 14 | X |
| Comparative Example 2 | 20 | 14 | X |

○: A homogenous aqueous suspension pesticide composition having excellent storage stability could be prepared.
X: A homogenous aqueous suspension pesticide composition having excellent storage stability could not be prepared.

EXAMPLE 3

1. Preparation of Ground Slurry 1.0 part of polyoxyethylene tristyrylphenyl ether phosphate was dissolved in 12.9 parts of water, and 6.1 parts of dry ground Halosulfuron-methyl was dispersed in the solution to obtain a ground slurry.

2. Preparation of Dispersion Medium 0.2 part of Proxel GXL (trade name of Zeneca Co.), 0.2 part of Welan gum (trade name of Kelco Biopolymers Co.), 0.9 part of citric acid monohydrate, 10.0 parts of propylene glycol and 0.2 part of Nopco 8034L (trade name of San Nopco Ltd.) were dispersed in 53.5 parts of water in the order named, and further 15.0 parts of a polyoxyethylene alkyl ether (HLB: 12.1, the mean molar ethylene oxide(EO) content: 7, the alkylmoiety: branched alkyl having 12 to 14 carbon atoms) was added to obtain a dispersion medium.

3. Preparation of Aqueous Suspension Formulation

A homogenous aqueous suspension formulation having excellent storage stability was obtained by mixing the above ground slurry and the dispersion medium in a ratio of 1:4. The viscosity of the obtained aqueous suspension formulation was 338 mPaS.

Comparative Example 3

An aqueous suspension formulation was prepared in the same manner as in Example 3 except that the amount of the polyoxyethylene alkyl ether was reduced from 15.0 parts to 7.5 parts and the amount of water was increased by that reduction.

Comparative Example 4

An aqueous suspension formulation was prepared in the same manner as in Example 3 except that the amount of the polyoxyethylene alkyl ether was reduced from 15.0 parts to 3.8 parts and the amount of water was increased by that reduction.

Test Example 1

A plastic pot having a diameter of 12 cm was filled with soil and cleavers(Galium aparine) seeds were sowed in the soil. The aqueous suspension formulations of Example 3 and Comparative Example 3 and 4 were sprayed on cleavers of four-leaf stage in an amount of 0.4 g per are (g/a.), calculated as pesticidally active ingredient Halosulfuron-methyl. The amount of the solution sprayed was 2.5 liters per are (1/a.). The herbicidal effect of Halosulfuron-methyl on cleavers was observed and evaluated 21 days after spraying. The results are shown in Table 2.

TABLE 2

| Herbicidal effect on cleavers | | |
|---|---|---|
| | Content of polyoxyethylene alkyl ether in formulation (wt %) | Observation evaluation |
| Example 3 | 15.0 | 90 |
| Comparative Example 3 | 7.5 | 77 |
| Comparative Example 4 | 3.8 | 63 |

Observation evaluation: 0 (no effect) to 100 (complete death)

Test Example 2

A plastic pot having a diameter of 12 cm was filled with soil and the tuber of purple nutsedge(Cyperus rotundus) was transplanted in the pot. When the purple nutsedge grew 15 cm in height, the aqueous suspension formulations of Example 3 and Comparative Example 3 and 4 were, sprayed on it in an amount of 0.5 g per are (g/a.), calculated as pesticidally active ingredient Halosulfuron-methyl.

The amount of the solution sprayed was 2.5 liters per are (1/a.). The herbicidal effect of Halosulfuron-methyl on the purple nutsedge was observed and evaluated 21 days after spraying. The results are shown in Table 3.

TABLE 3

| Herbicidal effect on purple nutsedge | | |
|---|---|---|
| | Content of polyoxyethylene alkyl ether in formulation (wt %) | Observation evaluation |
| Example 3 | 15.0 | 92 |
| Comparative Example 3 | 7.5 | 78 |
| Comparative Example 4 | 3.8 | 65 |

Observation evaluation: 0 (no effect) to 100 (complete death)

EXAMPLE 4

1. Preparation of Ground Slurry 0.5 part of a polyoxyethylene-polyoxypropylene block copolymer (molecular weight: about 20,000, weight ratio of ethylene oxide to propylene glycol: 8:2) and 0.1 part of FS Antifoam CE (trade name of silicone defoamer manufactured by Dow Corning Asia Co.) were dissolved in 14.0 parts of water, and 5.4 parts of Quizalofop-p-ethyl was dispersed in the solution and ground with a sand grinder (of AIMEX Co.) using 300 g of glass beads having a diameter of 1.0 to 1.5 mm at a revolution of 2,000 rpm by maintaining the temperature of cooling water at 10 to 15° C. and the temperature of the product at 10 to 20° C. for 120 minutes to obtain a ground slurry.

2. Preparation of Dispersion Medium 20.0 parts of a polyoxyethylene alkyl ether (HLB: 13.3, the mean molar ethylene oxide (EO) content: 9, the alkyl moiety: branched alkyl having 12 to 14 carbon atoms), 0.1 part of Veegum Granule (trade name of R. T. Vanderbirt Co.), 0.2 part of Kelzan ASX (trade name of Kelco Biopolymers Co.) and 0.2 part of Proxel GXL (trade name of Zeneca Co.) were dispersed in 54.6 parts of water in the order named, and further 5 parts of propylene glycol was added to obtain a dispersion medium.

3. Preparation of Aqueous Suspension Formulation

The above ground slurry and the above dispersion medium were mixed in a ratio of 1:4 to obtain a homogeneous aqueous suspension formulation having excellent storage stability. The viscosity of the obtained aqueous suspension formulation was 267 mPaS.

Comparative Example 5

An aqueous suspension formulation was prepared in the same manner as in Example 4 except that 20.0 parts of a polyoxyethylene alkylether (HLB: 13.3, the mean molar ethylene oxide(EO) content: 9, the alkyl moiety: branched alkyl having 12 to 14 carbon atoms) was changed to water. The viscosity of the obtained aqueous suspension formulation was 237 mPaS.

Test Example 3

The aqueous suspension formulations of Example 4 and Comparative Example 5 were sprayed over a beet field where barnyard grass(Echinochloa crus-gali) grew in an amount of 125 mg per are (mg/a.) in terms of Quizalofop-p-ethyl which is a pesticidally active ingredient. The herbicidal effects of the formulations upon the barnyard grass were observed and examined 20 days after spraying. The results are shown in Table 4.

TABLE 4

Herbicidal effect on barnyard grass

| | Content of polyoxyethylene alkyl ether in formulation (wt %) | Observation evaluation |
|---|---|---|
| Example 4 | 20 | 100 |
| Comparative Example 5 | 0 | 77 |

Observation evaluation: 0 (no effect) to 100 (complete death)

EXAMPLE 5
Preparation of Emulsifiable Concentrate 16.7 parts of a polyoxyethylene alkyl ether (HLB: 12.4, the mean molar ethylene oxide (EO) content: 4 to 12, the alkyl moiety: linear alkyl having 12 carbon atoms) and 8.3 parts of alkylbenzenesulfonic acid were mixed with 49.6 parts of Solvesso 150 (of Exxon chemical Co.) and 20.0 parts of Solvesso 200 (of Exxon chemical Co.) and further 5.4 parts of Quizalofop-p-ethyl was added to obtain a homogeneous emulsifiable concentrate having excellent storage stability.

Comparative Example 6

An emulsifiable concentrate was prepared in the same manner as in Example 5 except that the amount of the polyoxyethylene alkyl ether was reduced from 16.7 parts to 8.4 parts and the amount of alkylbenzenesulfonic acid was reduced from 8.3 parts to 4.2 parts and the amount of the Solvesso 150 (of Exxon Chemical Co.) was increased by that reduction.

Comparative Example 7

An emulsifiable concentrate was prepared in the same manner as in Example 5 except that the amount of the polyoxyethylene alkyl ether was reduced from 16.7 parts to 4.2 parts, the amount of alkylbenzenesulfonic acid was reduced from 8.3 parts to 2.1 parts and the amount of the Solvesso 150 (of Exxon Co.) was increased by that reduction.

Test Example 4

A plastic pot having a diameter of 12 cm was filled with soil and green foxtail (Setaria viridis) seeds were sowed in the soil. Three weeks after the seeds were sowed, the emulsifiable concentrates of Example 5 and Comparative Example 6 and 7 were sprayed on it in an amount of 0.5 g per are (g/a.), calculated as pesticidally active ingredient Quizalofop-p-ethyl.

The amount of the solution sprayed was 2.5 liters per are (l/a.). The herbicidal effect of the Quizalofop-p-ethyl on each green foxtail was observed and evaluated 21 days after spraying. The results are shown in Table 5.

TABLE 5

Herbicidal effect on green foxtail

| | Content of polyoxyethylene alkyl ether in formulation (wt %) | Observation evaluation |
|---|---|---|
| Example 5 | 16.7 | 100 |
| Comparative Example 6 | 8.4 | 86 |
| Comparative Example 7 | 4.2 | 75 |

Observation evaluation: 0 (no effect) to 100 (complete death)

Test Example 5

A biological test was conducted using spray solutions prepared by adding polyoxyethylene alkyl ethers having different HLB values to a herbicide spray solution. The polyoxyethylene alkyl ethers used in Test Example 5 and Test Example 6 are shown in Table 6.

TABLE 6

Polyoxyethylene alkyl ethers used in Tests

| No. | HLB | Mean molaer ethylene oxide content | Type of alkyl moeity |
|---|---|---|---|
| 1 | 9.7 | 4 | Linear, 12 to 14 carbon atoms |
| 2 | 12.1 | 7 | Branched, 12 to 14 carbon atoms |
| 3 | 12.9 | 8 | Linear, 12 to 14 carbon atoms |
| 4 | 13.3 | 9 | Branched, 12 to 14 carbon atoms |
| 5 | 13.4 | 9 | Linear, 12 to 13 carbon atoms |

Biological tests were conducted on velvetleaf (Abutilon theophrasti) using spray solutions prepared by adding polyoxyethylene alkyl ethers having different HLB values to a spray solution of 75% water dispersible granules of Halosulfuron-methyl. To confirm a difference in effect between the polyoxyethylene alkyl ethers, the tests were carried out using a lower concentration of Halosulfuron-methyl than usual. A plastic pot having a diameter of 12 cm was filled with soil, and velvetleaf seeds were sowed in the soil. The solutions were sprayed on velvetleaf of five-leaf stage in an amount of 0.1 g per are (g/a.), calculated as pesticidally active ingredient Halosulfuron-methyl. The amount of the solution sprayed was 2 liters per are (l/a.)and 1,000 ppm of a the polyethylene alkyl ethers were added to the solution. Herbicidal effects were observed and evaluated 27 days after spraying. The results are shown in Table 7.

TABLE 7

Herbicidal effect on Halosulfuron-methyl on velvetleaf

| polyoxyethylene alkyl ether | HLB | Observation evaluation |
|---|---|---|
| No. 1 | 9.7 | 63 |
| No. 2 | 12.1 | 70 |
| No. 4 | 13.3 | 80 |
| Not added | — | 40 |

Observation evaluation: 0 (no effect) to 100 (complete death)

Test Example 6

Biological tests were conducted on crabgrass(Digitaria ciliaris) using spray solutions prepared by adding polyoxyethylene alkyl ethers having different HLB values to a spray solution of 40% suspension concentrates of Quizalofop-p-ethyl. A plastic pot having a diameter of 12 cm was filled with soil, and crabgrass seeds were sowed in the soil. The solutions were sprayed on in an amount of 125 mg per are (mg/a.), calculated as pesticidally active ingredient Quizalofop-p-ethyl, 3 weeks after the seeds were sowed. The amount of the solution sprayed was 2.5 liters per are (l/a.) and 125 ppm of the polyoxyethylene alkyl ethers were added to the solution. Herbicidal effects on crabgrass were observed and evaluated 21 days after spraying. The results are shown in Table 8.

TABLE 8

Herbicidal effect on Quizalofop-p-ethyl on crabgrass

| Polyoxyethylene alkyl ether | HLB | Observation evaluation |
|---|---|---|
| No. 1 | 9.7 | 85 |
| No. 2 | 12.1 | 98 |
| No. 3 | 12.9 | 99 |
| No. 5 | 13.4 | 98 |
| Not added | — | 25 |

Observation evaluation: 0 (no effect) to 100 (complete death)

The present invention provides a liquid pesticide composition which has an improved biological effect of a pesticidally active ingredient, is homogeneous and has excellent storage stability by containing a polyoxyethylene alkyl ether having a specific HLB value to a liquid pesticide composition in high concentration.

What is claimed is:

1. A liquid pesticide composition comprising a pesticidally active ingredient and a polyoxyethylene alkyl ether which has the following features (a) and (b):
   (a) an HLB value of 6 to 13.5 and (b) a content of 10 to 50 wt % based on the liquid pesticide composition.

2. The liquid pesticide composition according to claim 1, which is an aqueous suspension formulation.

3. The liquid pesticide composition according to claim 1, which is an emulsifiable concentrate.

4. The liquid pesticide composition according to claim 1, wherein the content of the polyoxyethylene alkyl ether is 15 to 30 wt % based on the liquid pesticide composition.

5. The liquid pesticide composition according to claim 1, wherein the pesticidally active ingredient is a herbicide.

6. The liquid pesticide composition according to claim 5, wherein the herbicide has foliar treating activity.

7. The liquid pesticide composition according to claim 6, wherein the herbicide having foliar treating activity is a phenoxypropionic acid herbicide.

8. The liquid pesticide composition according to claim 7, wherein the phenoxypropionic acid herbicide is Quizalofop-ethyl.

9. The liquid pesticide composition according to claim 6, wherein the herbicide having foliar treating activity is a sulfonylurea herbicide.

10. The liquid pesticide composition according to claim 9, wherein the sulfonylurea herbicide is Halosulfuron-methyl.

11. A liquid pesticide composition comprising a pesticidally active ingredient and a polyoxyethylene alkyl ether which has the following features (a) and (b):
    (a) an HLB value of 8 to 13.5 and (b) a content of 10 to 50 wt % based on the liquid pesticide composition.

12. The liquid pesticide composition according to claim 11, wherein the pesticidally active ingredient is a herbicide.

13. The liquid pesticide composition according to claim 11, which is an aqueous suspension formulation.

14. The liquid pesticide composition according to claim 11, which is an emulsifiable concentrate.

15. The liquid pesticide composition according to claim 11, wherein the content of the polyoxyethylene alkyl ether is 15 to 30 wt % based on the liquid pesticide composition.

16. A liquid pesticide composition comprising a pesticidally active ingredient and a polyoxyethylene alkyl ether which has the following features (a) and (b):
    (a) an HLB value of 11 to 13.5 and (b) a content of 10 to 50 wt % based on the liquid pesticide composition.

17. The liquid pesticide composition according to claim 16, wherein the pesticidally active ingredient is a herbicide.

18. The liquid pesticide composition according to claim 16, which is an aqueous suspension formulation.

19. The liquid pesticide composition according to claim 16, which is an emulsifiable concentrate.

20. The liquid pesticide composition according to claim 16, wherein the content of the polyoxyethylene alkyl ether is 15 to 30 wt % based on the liquid pesticide composition.

* * * * *